United States Patent
Pell et al.

(10) Patent No.: US 11,529,311 B2
(45) Date of Patent: *Dec. 20, 2022

(54) METHOD OF USING NEBULIZED ALCOHOL FOR ANALGESIA

(71) Applicant: BN Intellectual Properties, Inc., St. Petersburg, FL (US)

(72) Inventors: Donald M. Pell, St. Petersburg, FL (US); Frank Caiazzo, St. Petersburg, FL (US)

(73) Assignee: BN INTELLECTUAL PROPERTIES, INC., St. Petersburg, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/345,830

(22) Filed: Jun. 11, 2021

(65) Prior Publication Data

US 2022/0233436 A1    Jul. 28, 2022

Related U.S. Application Data

(60) Provisional application No. 63/142,904, filed on Jan. 28, 2021.

(51) Int. Cl.
| | | |
|---|---|---|
| *A61K 9/00* | (2006.01) | |
| *A61K 31/045* | (2006.01) | |
| *A61M 11/00* | (2006.01) | |
| *A61P 25/04* | (2006.01) | |

(52) U.S. Cl.
CPC .......... *A61K 9/0078* (2013.01); *A61K 31/045* (2013.01); *A61M 11/005* (2013.01); *A61P 25/04* (2018.01); *A61M 2205/0294* (2013.01); *A61M 2205/3327* (2013.01); *A61M 2205/50* (2013.01)

(58) Field of Classification Search
CPC . A61K 9/0078; A61K 31/045; A61M 11/005; A61M 2205/3327; A61P 25/04
See application file for complete search history.

(56) References Cited

U.S. PATENT DOCUMENTS

| | | | |
|---|---|---|---|
| 6,098,620 A | 8/2000 | Lloyd | |
| 7,360,536 B2 * | 4/2008 | Patel | A61M 15/0065 128/200.14 |
| 10,098,379 B2 | 10/2018 | von Borstel | |
| 10,729,648 B2 | 8/2020 | Pell | |
| 10,765,817 B2 | 9/2020 | Boyden | |
| 10,786,485 B1 * | 9/2020 | Cole | A61K 45/06 |
| 2004/0256745 A1 | 12/2004 | Simler | |
| 2008/0295831 A1 | 12/2008 | Svehaug | |
| 2016/0045682 A1 * | 2/2016 | Boyden | A61M 11/02 128/200.19 |
| 2020/0261665 A1 | 8/2020 | Pell | |

FOREIGN PATENT DOCUMENTS

| | | |
|---|---|---|
| CN | 210409156 U | 4/2020 |
| CN | 111297836 A | 6/2020 |
| WO | 1996013293 A1 | 5/1996 |
| WO | WO 2017111668 * | 6/2017 |
| WO | WO 2017111668 A * | 6/2017 |

OTHER PUBLICATIONS

Zhang et al., Inhalation of alcohol vapor driven by oxygen in a useful therapeutic method for postoperative alcohol withdrawal syndrome in a patient with esophageal cancer; a case report; Alcohol and Alcoholism, vol. 46, No. 4, pp. 424-426. (Year: 2011).*
Ari; Jet, Ultrasonic and Mesh Nebulizers: an Evaluation of Nebulizers for better clinical outcomes; Eurasian J Pulmonol 2014 16: 1-7 (Year: 2014).*
Buddy T; The danger of using alcohol for pain relief; Verywell mind (Year: 2020).*
Gameiro et al; Effects of ethanol on deep pain evoked by formalin injected in TMJ of rat; Science direct, Life Sciences 73 (2003) 3351-3361. (Year: 2003).*
The Good and the Bad of Vaporizing and Inhaling Alcohol, Today I Found Out—Feed Your Brain, pp. 1-14, retrieved from: https://www.todayifoundout.com/index.php/2014/04/good-bad-vaporizing-inhaling-alcohol/ on May 11, 2021.
Sisson, J.H., Alcohol and Airways Function in Health and Disease, HHS Public Access, Alcohol, Aug. 2007, 41(5), 293-307, pp. 2-24, retrieved from: https://www.ncbi.nlm.nih.gov/pmc/articles/PMC2081157/on May 11, 2021.
MacLean et al., R.R., Inhalation of Alcohol Vapor: Measurement and Implications, HHS Public Access, Clcohol Clin Exp Res, Feb. 2017, 41(2), 238-250, pp. 2-22, retrieved from: https://www.ncbi.nlm.nih.gov/pmc/articles/PMC6143144/ on May 11, 2021.
C. Thompson T, Oram C, Correll CU, Tsermentseli S, Stubbs B, Analgesic effects of alcohol: A systematic review and meta-analysis of controlled experimental studies in healthy participants, Journal of Pain (2017), doi: 10.1016/j.pain.2016.11.009.

* cited by examiner

*Primary Examiner* — Mina Haghighatian
(74) *Attorney, Agent, or Firm* — Hauptman Ham, LLP

(57) ABSTRACT

A method of regulating pain in a patient includes operations of measuring a patient pain level, determining a dose of ethanol which does not trigger alcohol intolerance or intoxication, delivering the dose of ethanol to the patient by inhalation from an active mesh nebulizer at a repeated interval, measuring the pain level of the patient at a monitoring interval, and determining, based on the patient pain level, whether to adjust the ethanol dose. The dose of ethanol is delivered in the form of particles of nebulized liquid having a diameter ranging from about 0.5 μm to about 5.0 μm, which are rapidly absorbed into the bloodstream of a patient and delivered to the brain.

20 Claims, 2 Drawing Sheets

METHOD OF USING NEBULIZED ALCOHOL FOR ANALGESIA

PRIORITY CLAIM AND CROSS REFERENCE

This application claims priority to the provisional U.S. Patent Application 63/142,904 titled "METHOD OF USING NEBULIZED ALCOHOL FOR ANALGESIA" and filed on Jan. 28, 2021, which is incorporated herein by reference.

The present disclosure is related to U.S. patent application Ser. No. 17/100,566 titled "NEBULIZER DELIVERY SYSTEMS AND METHODS" and filed on Nov. 20, 2020, which is incorporated herein by reference. The present disclosure is also related to U.S. patent application Ser. No. 16/547,072 titled "METHOD OF DELIVERING PHARMACEUTICAL PRODUCTS" and filed on Aug. 21, 2019, which is incorporated herein by reference.

BACKGROUND

The use of opioid medications for pain relief is associated with many adverse health conditions. Opioid medications frequently impact bowel and kidney function and mental acuity. Opioid use is associated with medication tolerance, as a patient becomes habituated to an opioid medication and doses of increasing size are used to achieve pain relief over time. Opioid medications are misused by many persons in order to seek relief for physical or emotional pain. Many illegal opioid medications are substituted for legally-prescribed opioid medications after users become addicted to opioid medications.

DETAILED DESCRIPTION

Figure 1:
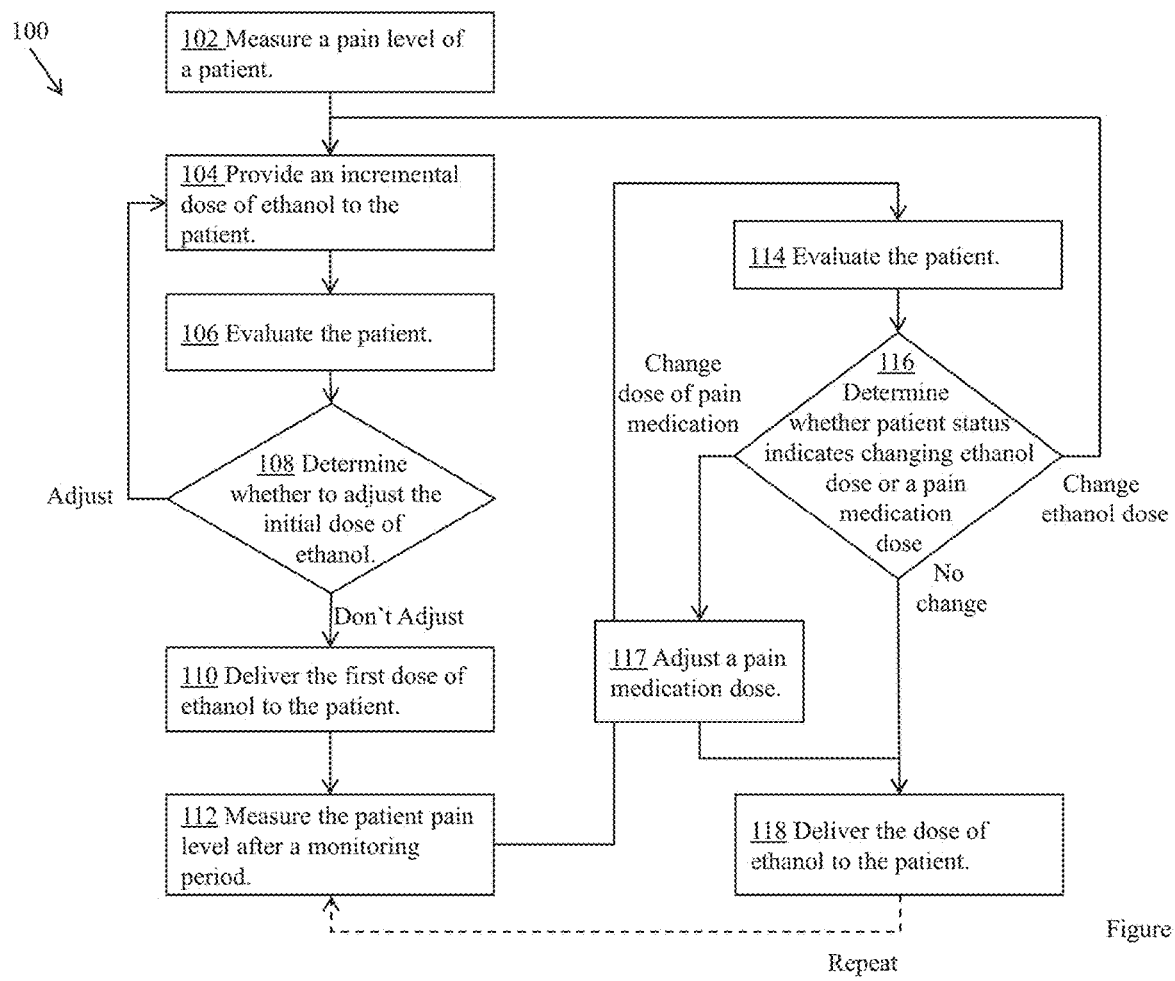
FIG. 1 is a flow diagram of a method of delivering alcohol for analgesia, in accordance with some embodiments.

The following disclosure provides many different embodiments, or examples, for implementing different features of the provided subject matter. Specific examples of components, values, operations, materials, arrangements, or the like, are described below to simplify the present disclosure. These are, of course, merely examples and are not intended to be limiting. Other components, values, operations, materials, arrangements, or the like, are contemplated. The present disclosure may repeat reference numerals and/or letters in the various examples of operations. This repetition is for the purpose of simplicity and clarity and does not in itself dictate a relationship between the various embodiments and/or configurations discussed.

Analgesic compounds used for pain relief operate in the body by mechanisms according to the chemical structure of each analgesic compound. Many analgesic compounds are available over the counter (OTC) for self-administration by a person experiencing pain. For example, non-steroidal anti-inflammatory medications are used to treat minor pain associated with swelling or inflammation in the body by, e.g., reducing the amount of inflammation experienced by a person. Some analgesic compounds with stronger pain-relieving effects operate on the nervous system and are typically available only by prescription under supervision by a healthcare provider. Supervision by a healthcare provider helps a person avoid addiction and/or other negative health effects (nausea, constipation, as well as depression and over-sedation) from such analgesic compounds. For example, long-term use of opioid medications is associated with medication tolerance, where a person is habituated to a first dose of medication, and larger doses are used over time in order to achieve a same degree of pain relief as was initially experienced with the first dose of medication. For some people, habituation is a first step to addictive behavior. For some people, OTC analgesics, prescribed analgesic compounds, and combinations thereof are not fully effective at treating pain, and other pain relief solutions are sought out for relief. For some people, seeking pain relief after other analgesics have been ineffective is a path to addictive behavior.

Ethyl alcohol (ethanol, or "alcohol") is a central nervous system (CNS) depressant. Many people self-medicate for pain relief by drinking to consume ethanol. Alcoholism is a common condition for people experiencing significant pain without effective relief from other analgesic compounds. According to the organization Alcoholics Anonymous, 28 percent of the organization's membership uses ethanol for pain relief (analgesia) because other pain remedies have failed to accomplish significant or satisfying pain relief, or because the other remedies accomplish pain relief accompanied by undesirable side effects. For example, many retired professional athletes have stated that consuming large quantities of ethanol is the only means by which they get relief from chronic trauma-induced pain. Pain relief associated with drinking large quantities of ethanol is often achieved when a drinker has become intoxicated. Drinking ethanol to the point of intoxication is associated with many adverse health effects, including liver cirrhosis, impaired memory, and slowed response times.

The concurrent use of opioid medications for pain relief and consumption of ethanol is not recommended by many healthcare providers because both opioid medications and ethanol are central nervous system (CNS) depressants. Patient use of opioid medications is accompanied by recommendations for patients to avoid drinking alcohol because elevated risk of slower respiration.

The use of opioid medications and (drinking) ethanol are understood to achieve pain relief in similar ways: by triggering increased production of the neurotransmitters.

According to theory and belief, ethanol, when delivered according to the method disclosed herein, produces pain relief by a different mechanism than opioid medications, and without the negative health risks and side effects of opioid medication use. According to theory and belief, doses of ethanol delivered by an active mesh nebulizer which produces particles having particle diameters in the range of 0.5 micrometers (μm) to 5.0 μm, are effective at achieving pain relief in patients, with or without the use of other analgesic compounds (e.g., opioid medications). In some embodiments, the nebulized ethanol delivered by an active mesh nebulizer which produces particles having particle diameters in the range of about 0.5 μm to about 5.0 μm are able achieve complete pain relief for chronic pain or acute pain in patients without other analgesics, including, e.g., opioid medication. Further, in some embodiments of the method described herein, the nebulized ethanol is delivered to a patient who is taking other analgesics, including, e.g., opioid medications, to achieve pain relief, so that the patient is able to taper the dose of the other analgesic, until a patient ceases taking the other analgesic. The use of nebulized alcohol for pain relief as described herein does not appear to have been previously disclosed in the literature of pain management.

FIG. 1 is a flow diagram of a method 100 of delivering alcohol to a patient, in accordance with some embodiments. In operation 102 of method 100, a patient pain level is measured or evaluated to determine one or more parameters of a pain management plan. In some embodiments, the measuring a patient pain level is determined by a healthcare provider at a physician's office as part of creating the pain management plan. In some embodiments, a patient performs self-evaluation of his or her pain level, without supervision by a healthcare provider. In some embodiments, the initial pain level serves as a baseline for a pain management plan. In some embodiments, the pain management plan provides pain relief by administering only inhaled nebulized ethanol solution as described herein. In some embodiments, the pain management plan is used in combination with other analgesic compounds or the use of rehabilitative or medical treatments. Measuring a patient pain level before administering a dose of ethanol to the patient provides a baseline for estimating the size of the initial dose of ethanol to be delivered to the patient.

Due diligence is exercised in performing operations 104, 106, and 108, as described below, to monitor patient health, and to avoid recurrence of patient pain during the pain management plan. In some embodiments, operations 104, 106, and 108 are each performed a single time in order to identify the initial dose of ethanol to achieve pain relief. In some embodiments, operations 104, 106, and 108 are performed multiple times in order to determine the initial dose of ethanol to achieve pain relief.

The term "initial dose" refers to a quantity of ethanol which is used for an evaluation period to determine whether a patient experiences pain relief for the dose, and/or exhibits symptoms of intolerance or intoxication. The term "incremental dose" refers to a quantity of ethanol which is delivered from an active mesh nebulizer during the span of a single vibrational period of the active mesh nebulizer for inhalation during a single breath by a person experiencing pain. As further described below, an incremental dose is delivered over a span of about 2-6 seconds (the duration of a single vibrational period of an active mesh nebulizer for a single breath by a person). In some embodiments, the initial dose is the same as one incremental dose. In some embodiments, the initial dose is the sum of several incremental doses, at which point a person is able to report pain relief (reduction or elimination of pain). For purposes of the present disclosure, the terms "first dose," "second dose," and so forth, indicate discrete quantities of ethanol to be delivered to a patient at a repeated interval in a plume of particles of ethanol solution. In some embodiments, the first dose is the same size as the initial dose determined to be effective at achieving pain relief, and refers to the dose of ethanol delivered at a repeated interval to maintain pain relief. A second dose refers to a dose of ethanol different from the first dose, in response to a person's changed experience of pain relief. In some embodiments, the second dose is larger than the first dose. In some embodiments, the second dose is smaller than the first dose. Subsequent doses of ethanol (e.g., a third dose, a fourth dose, and so forth) indicate changes in the dose of ethanol with respect to the dose delivered immediately prior to the currently-administered dose.

Method 100 includes an operation 104, wherein an incremental dose of ethanol is provided to the patient. The incremental dose of ethanol provided to a patient comprises the ethanol produced by an active mesh nebulizer, as described below, for the duration of a single vibrational period of the active mesh or grid of the nebulizer, for inhalation during a single breath.

According to some embodiments of operation 104, a healthcare provider or a user of an active mesh nebulizer places an ethanol solution in contact with the active mesh of the active mesh nebulizer and triggers vibration of the piezoelectric grid in contact with the ethanol solution to produce a plume of particles of ethanol solution (the incremental dose) which is inhaled by the patient and absorbed into the bloodstream.

The active mesh nebulizer, or other nebulizer, which produces the incremental dose of ethanol is similar to the active mesh nebulizer as described in U.S. patent application Ser. No. 17/100,566 titled "NEBULIZER DELIVERY SYSTEMS AND METHODS" and filed on Nov. 20, 2020. The active mesh nebulizer described therein is configured to produce a plume of particles or a cloud of droplets by vibrating an active mesh or grid attached to a piezoelectric element operating at between about 50 kHz and about 400 kHz. The plume of particles is generated as a first side of the vibrating active mesh or grid presses against the surface of the liquid in the active mesh nebulizer, and the vibrations of the active mesh or grid cause some of the liquid to move through the openings in the active mesh or grid, into the air at a second side of the active mesh or grid. A cover (e.g., a mouthpiece or mask) fitted over the second side of the active mesh or grid prevents the plume of particles from randomly dispersing in the air, such that the plume is contained until inhaled by a patient. In some embodiments, the plume is produced during an inhalation (inspiratory event) which begins before, and ends after, the duration of the plume production. The cover is shaped, and is sufficiently large, such that the plume of particles does not condense on the inner surface of the cover, and has [1] an opening for particles to exit the cover during inhalation, and [2] air inlets to facilitate smooth airflow into the cover and entrainment of the particles during inhalation.

Alveoli in the lungs are able to admit particles of ethanol solution which have a diameter smaller than about 5.0 μm. The distribution of particle diameters in the plume of particles allows some or all of the particles of the plume of particles to enter alveoli in the lungs without striking bronchial walls or other lung tissue during inhalation.

The amphiphilic nature of ethanol allows for rapid absorption of the ethanol solution both [1] into the bloodstream in the lungs, and [2] into the brain tissue from capillaries in the brain, e.g., once a portion of the ethanol reaches the brain. A portion (about 20%) of the person's bloodflow from the lungs and heart is directed to the head and brain, and about 80% is directed to the rest of a person's body. Ethanol in the portion of bloodflow to the person's brain reaches the brain in about 10 seconds. Upon reaching the brain, the ethanol of the incremental dose begins to triggers pain relief without symptoms or side effects of alcohol intoxication. In some patients, the ethanol also produces a sensation of mild euphoria or drowsiness.

An amphiphilic molecule is a molecule which has both hydrophilic and hydrophobic components. Amphiphilic molecules are readily dissolved in water, and are also attracted to lipid layers of cells and fatty body tissues. Thus, the hydrophilic character of ethanol hydroxyl group promotes rapid absorption of the ethanol into the bloodstream, and the hydrophobic character of the ethyl moiety promotes rapid absorption of the ethanol into brain tissue. According to theory and belief, the ethanol is rapidly absorbed by at least myelin sheathes of neurons.

According to theory and belief, the rapid uptake of the ethanol by the brain produces a state of receptor saturation for the affected neurons, resulting in pain relief. Further, because of the reduced quantity of ethanol delivered (e.g., in comparison to drinking ethanol), a patient avoids symptoms of intolerance or intoxication.

In some embodiments of the method, an initial dose of ethanol is a single incremental dose of ethanol, and produces pain relief. In some embodiments, the initial dose comprises multiple incremental doses delivered to a person to achieve pain relief. In some embodiments, the pain relief is partial pain relief. In some embodiments, the pain relief is complete pain relief.

An active mesh nebulizer as described herein, is able to produce plumes of particles from a variety of solutions of many kinds of pharmaceutical products, including solutions which contain pure ethanol, ethanol with water, and combinations of ethanol and other pharmaceutical compounds, with and without water.

The initial dose of ethanol delivered to a patient is determined as a function of the patient's pain response (e.g., the degree of pain relief afforded the patient from the treatment) and/or the patient's physiology (e.g., age, weight, biological sex), previous alcohol history, alcohol tolerance, and so forth. In some embodiments, the initial dose is determined by a medical provider, and programmed into the active mesh nebulizer, or into an electronic device which is accessed by the active mesh nebulizer to read the initial dose (or, the first dose) information for the patient or user.

In some embodiments, the vibrational time of the active mesh is determined based on the plume production rate of the active mesh of the active mesh nebulizer for various sets of operational parameters of the active mesh nebulizer, and the vibrational time is accessed by a controller circuit of the active mesh nebulizer for delivering the dose of ethanol. In some embodiments, the vibrational time calculated to deliver an initial dose of the ethanol solution ranges from about 1 second to about 10 seconds. In some embodiments, the vibrational time calculated to deliver a dose of the ethanol solution ranges from about 10 seconds to about 20 seconds. Vibrational times smaller than about 1 second are not indicated for use in delivering medications from an active mesh nebulizer because of occasional uneven response of the active mesh to the piezoelectric grid which stimulates the production of the plume of particles. Vibrational times greater than about 20 seconds are generally associated with excess delivery of ethanol solution (e.g., ethanol) given the rapid response of the brain and body to the delivered ethanol solution and the rapid onset of pain relief.

In some embodiments, the controller is configured to monitor the vibrational time of the active mesh of the active mesh nebulizer to determine that the dose of ethanol solution which has been delivered to the patient by the active mesh nebulizer. In some embodiments, the monitoring includes monitoring a single vibrational period of the active mesh nebulizer during a single inhalation period for delivery of an initial dose of ethanol solution. In some embodiments, the monitoring includes monitoring multiple vibrational periods of the active mesh nebulizer over several inhalation periods for delivery of an initial dose of ethanol solution.

In some embodiments, the controller is configured to determine whether the delivered dose of ethanol solution and the calculated or programmed dose of ethanol solution are the same amount of ethanol solution.

In some embodiments, the controller is configured to prevent, upon determining that the delivered dose of ethanol solution and the calculated or programmed dose of ethanol solution are the same amount of ethanol solution, additional activation of the active mesh nebulizer, and additional delivery of ethanol solution to the patient in a plume of particles, until a prescribed waiting or delay period between delivering doses of the ethanol solution has elapsed.

Doses of ethanol are delivered by nebulizing an ethanol solution containing at least ethanol and water, as described herein. In some embodiments, other ingredients are also included in the nebulized source solution (e.g., flavorings and so forth) in order to promote adherence to the pain regulation plan by making the alcohol treatment more pleasant for the patient. In some embodiments, the ethanol solution consists of ethanol and water with no flavoring compound added thereto. In some embodiments, the ethanol solution comprises ethanol and water and an optional flavoring compound added thereto to modify the taste or scent of the ethanol solution during treatment.

According to some embodiments, the ethanol solution comprises between about 25% and 100% ethanol. According to some embodiments, the ethanol solution comprises between about 50% ethanol and 100% ethanol. According to some embodiments, the ethanol solution comprises between about 75% ethanol and 100% ethanol. According to some embodiments, the ethanol solution comprises between about 90% ethanol and 100% ethanol.

An ethanol solution having low ethanol concentration (e.g., between about 25% and about 50% ethanol) is suitable for persons having greater sensitivity to ethanol-induced pain relief, or persons who have little or no prior history of ethanol consumption, or for persons having smaller body mass or less severe pain relief issues. An ethanol solution having a higher concentration of ethanol (e.g., between 50% and 100% ethanol) is able to produce pain relief in a user more quickly, and is easier to deliver (e.g., using fewer inhalations) than a solution having a lower concentration (e.g., <50% by volume) of ethanol. An ethanol solution having a concentration of between about 75% and 100% ethanol, or between about 90% and 100% ethanol, is suitable for pain relief in patients with more severe pain who seek faster pain relief from, e.g., recurring chronic pain.

According to some embodiments, an ethanol solution comprises ethanol, in a volume described above, with a remainder of the ethanol solution being water (e.g., 75% by volume ethanol, 25% by volume water). In some embodiments, an ethanol solution comprises ethanol, in a volume described above, with a remainder of the ethanol solution being a combination of water, and a secondary pharmaceutical (e.g., 75% by volume ethanol, and 25% by volume of [water+secondary pharmaceutical]). In some embodiments, the second pharmaceutical comprises a medication for relieving headaches or migraines.

In some embodiments of the method described herein, a concentration of ethanol in the ethanol solution is selected according to a patient's tolerance for performing repeated inhalations from the active mesh nebulizer. In some embodiments of the method described herein, a concentration of ethanol in the ethanol solution is selected by a healthcare provider to deliver pain relief to a patient in a predetermined number of inhalations through the nostrils or the mouth. For patients with a high alcohol tolerance due to regular consumption of alcohol, pain relief is understood to be achieved by delivering a larger dose of ethanol than for patients with low alcohol tolerance (e.g., patient history includes little or no alcohol consumption). Ethanol solutions having a concentration of less than 25% ethanol by volume are less likely to be effective at treating patients to achieve pain relief because the patients are less likely to follow a treatment protocol with large numbers of inhalations to achieve a prescribed quantity of nebulized ethanol during the treatment, and are more likely to miss part of the inhalations due to inattention during the treatment.

For purposes of clarity, biological males are referred to hereinafter as men, and biological females are referred to hereinafter as women. Because men and women have different metabolic responses to alcohol consumption, some pain regulation plans factor a person's biological gender into the alcohol treatment dose sizes. In some embodiments, an initial dose delivered to a patient for nebulization is the same regardless of biological sex. In some embodiments, the pain regulation plan is performed in the presence of a health care provider, where the patient reports pain levels to the health care provider at immediately, and at repeated intervals (e.g., 1 minute, 2 minutes, 3 minutes after alcohol delivery from the nebulizer) until pain relief is achieved without alcohol intolerance or intoxication.

U.S. patent application Ser. No. 16/547,072 titled "METHOD OF DELIVERING PHARMACEUTICAL PRODUCTS" and filed on Aug. 21, 2019 describes a process of measuring and delivering a dose of a pharmaceutical product to a patient. For purposes of the present disclosure, a dose of ethanol delivered to a patient as part of a pain treatment in a pain regulation plan comprises a single quantity of alcohol delivered to a patient in a short period of time in one, or several sequential or near-sequential, inhalations, followed by a longer period of time (typically hours, or hundreds or thousands of inhalations) between doses.

A dose of ethanol is generated by activating the active mesh nebulizer as described below. An active mesh nebulizer is a medical device configured to deliver the ethanol solution to a patient as a plume of small particles inhaled into the lungs. In some embodiments, the active mesh nebulizer is configured to deliver the plume of droplets or particles of liquid to a user for treatment of lung tissue, or absorption into the body through the lungs for treatment of other tissues in a patient. An active mesh nebulizer is configured to receive and nebulize ethanol solutions from a vial or capsule containing the ethanol solution. The vial is configured to be replaced with a new vial from time to time.

The vial dispenses ethanol solutions of medication as an aerosol plume, or a plume of droplets or particles of liquid, according to the digitally stored instructions performed by the active mesh nebulizer. For further explanation of the digitally stored instructions to be performed by the active mesh nebulizer, see the description of FIG. 2, below.

The duration of the pain relief experienced by users is anticipated to vary according to the severity and nature of the pain experienced by the user of the active mesh nebulizer. In some embodiments of the method, the use of nebulized ethanol is anticipated to achieve pain relief for not less than 4 hours, and not greater than 18 hours. In some embodiments, pain relief is anticipated for not less than 6 hours and not greater than 12 hours. In some embodiments, a duration of pain relief is anticipated to increase in conjunction with patient use of non-steroidal anti-inflammatory medications. In some embodiments of the method, the use of nebulized ethanol in conjunction with opioids achieves pain relief, and the patient is able to reduce opioid medication consumption gradually under the supervision of a healthcare provider to avoid withdrawal symptoms associated with sudden cessation of opioid medication, until opioid medication use is halted completely.

An active mesh nebulizer is uniquely effective at generating a plume of particles or droplets of a liquid contained therein. Some particles have particle diameters ranging from 0.5 to 5 micrometers ($\mu m$). In some embodiments, up to 98% of the particles have particle diameters within the range of 0.5 $\mu m$ to 5.0 $\mu m$. Particles having a particle diameter outside the range of 0.5 $\mu m$ to 5.0 $\mu m$ are less effective at pain relief because such particles are not able to enter the alveoli for absorption into the bloodstream, and diffuse into the blood and other body tissues more slowly than the particles in the range of 0.5 $\mu m$ to 5.0 $\mu m$ are absorbed into the bloodstream. The plume of particles is readily inhaled by a patient without significant impact of the particles on the tissue of the lungs. In some embodiments, other distributions of particle diameters (e.g., from 0.5 $\mu m$ to 10 $\mu m$, or from 0.5 $\mu m$ to 20 $\mu m$, and so forth) are also effective at triggering pain relief.

The liquid in an active mesh nebulizer is converted into droplet form upon vibration of a piezoelectric active mesh, which vibrates at between 50 and 400 kHz, to force the liquid through small openings in the piezoelectric active mesh with each vibration. Droplets of liquid which are formed after the liquid is forced through the piezoelectric active mesh are directed into a mouthpiece for inhalation by a person using the active mesh nebulizer. The active mesh nebulizer forms droplets of the liquid therein without heating the liquid, which preserves chemical compounds dissolved in the liquid for delivery to a user upon inhalation. Droplets having a particle diameter of between 0.5 and 5.0 $\mu m$ are entrained with inhaled air deep into the lungs and absorbed through the alveoli into the bloodstream.

A unique and unexpected feature of delivering chemical compounds to a user through the lungs by inhaling droplets with diameters of between 0.5 and 5.0 $\mu m$ from an active mesh nebulizer is that chemical compounds which are so delivered have an unexpectedly large effect on the brain, despite the small total quantity of chemical compound which is so delivered. Particles having a diameter greater than about 5 microns have sufficient mass that, upon inhalation, the particles strike the walls of the mouth, throat, and upper branches of the lungs, where absorption rates are low, as compared to the absorption rates of inhaled droplets in the lower branches of the lungs and the alveolar sacs.

Venous blood traveling through the lungs to be oxygenated absorbs the chemical compounds delivered to the lungs, returns to the heart, and is then circulated throughout the body. Approximately 20% of the blood which exits the heart is directed to the brain, where the chemical compound absorbed therein is rapidly perfused into the brain tissue via the large surface area of the complex capillary network in the brain. Thus, a small concentration of a brain active chemical compound is able to achieve saturation, or near saturation, of the chemical receptors for that compound in the brain tissue, and trigger the anticipated brain effect of that brain active chemical compound.

For active mesh nebulizers which deliver particles or droplets of an ethanol solution to the brain by absorption through the lungs, the brain effect experienced by a person using the active mesh nebulizer is somewhat similar to the brain effect experienced by consuming (drinking) alcohol. Further, because of the efficiency of generating a brain effect with a brain-active chemical compound (e.g., ethanol) by the method of delivery described above, the concentrations of the brain-active chemical compound in the nebulizer solution, and the total dose of delivered compound to achieve the brain effect, are smaller than expected (see, e.g., the non-limiting example provided below for treating sinusitis with nebulized alcohol for one sample dose and treatment regimen, where the total delivered dose of 75% by volume ethanol solution is 0.08 ml). Further descriptions of treatments of a patient with an active mesh nebulizer using an alcohol-containing solution are provided below.

Because particles of ethanol solution with diameters of between 0.5 and 5.0 μm are entrained so efficiently into the deep lung, or alveolar tissue, there is no need to modify the pH of the solution to avoid triggering the cough reflex in a person using the active mesh nebulizer. Thus, a nebulizer solution has, in some embodiments, a pH ranging from about 3.5 to about 12 with no negative impact on the lungs or alcohol absorption when delivered from an active mesh nebulizer.

In operation 106 of method 100, a patient is evaluated for indications of pain relief and/or symptoms of alcohol intolerance. Symptoms of alcohol intolerance include: flushing, increased heart rate, and symptoms of reduced blood pressure, modified (as compared to a pre-evaluation level) levels of cognitive function or physical coordination, and so forth.

Pain relief and alcohol intolerance is evaluated by providing a patient a first dose (an incremental dose) of ethanol at the level or dose determined in operation 104, as described above. A dose of ethanol is delivered to a patient according to the methodology described in U.S. patent application Ser. No. 16/547,072 titled "METHOD OF DELIVERING PHARMACEUTICAL PRODUCTS" and filed on Aug. 21, 2019, using a device as described in U.S. patent application Ser. No. 17/100,566 titled "NEBULIZER DELIVERY SYSTEMS AND METHODS" and filed on Nov. 20, 2020.

In some embodiments, a patient indicates that he/she is experiencing partial pain relief, and the method proceeds to operation 108. In some embodiments the patient indicates that he/she is experiencing complete pain relief, and the method proceeds to operation 108.

In operation 108, based on a result of operation 106 (patient evaluation), a determination is made, by a healthcare provider, or by the patient, about whether to adjust the initial dose of ethanol for the patient to take to achieve a greater degree of pain relief.

In some embodiments, an initial dose of ethanol which produces the above-described pain relief effect is smaller than 1 ml of ethanol solution, having an alcohol concentration of 75% ethanol by volume (e.g., smaller than about 0.75 ml pure ethanol). In some embodiments, an initial dose of ethanol which produces the above-described pain relief effect is smaller than 0.5 ml of ethanol solution, having an alcohol concentration of 75% ethanol by volume (e.g., smaller than about 0.375 ml pure ethanol). In some embodiments, an initial dose of ethanol which produces the above-described pain relief effect is smaller than 0.2 ml of ethanol solution, having an alcohol concentration of 75% ethanol by volume (e.g., smaller than about 0.15 ml pure ethanol). In some embodiments, an initial dose of ethanol which produces the above-described pain relief effect is smaller than 0.1 ml of ethanol solution, having an alcohol concentration of 75% ethanol by volume (e.g., smaller than about 0.075 ml pure ethanol). In some embodiments, the balance of the ethanol solution is water (e.g., the solution is about 75% ethanol by volume and about 25% water by volume). In some embodiments, the balance of ethanol solution is water plus a secondary pharmaceutical to be co-delivered to the patient with the ethanol (e.g., the solution is about 75% ethanol by volume and the combination of water and the secondary pharmaceutical is about 25% by volume).

According to theory and belief, a patient experiencing a recurrence of chronic pain (e.g., injury to back, neck, muscles, joints, and so forth), is able to achieve pain relief with approximately 5 inhalations from an active mesh nebulizer, where each inhalation comprises a plume of particles from the active mesh nebulizer of about 3 second duration at a consumption rate (of the ethanol solution) of about 0.2 ml/minute.

The first dose of ethanol is set equal in size to the initial dose of ethanol (the repeated dose, of or the maintaining dose) which was determined to achieve pain relief and not induce alcohol intolerance (e.g., in one or more iterations of operations 104, 106, and 108). According to embodiments, an entirety of the droplets produced by the active mesh nebulizer are inhaled in order to consume the dose of ethanol. In some embodiments, a single inhalation suffices to consume the initial dose of ethanol. In some embodiments, multiple inhalations are used to consume the initial dose of ethanol. In some embodiments, inhalations are provided through a patient's mouth. In some embodiments, the inhalations are provided through a patient's nose.

In operation 110 of method 100, the first dose of ethanol is delivered to the patient with an active mesh nebulizer when pain relief begins to wane, and the patient pain returns (e.g., after several hours).

As described above, the dose of ethanol is delivered to a patient with an active mesh nebulizer in order to produce droplets of ethanol solution which have diameters within the range of 0.5 µm to 5 µm. In some embodiments, the percentage of particles having diameters within the range of 0.5 µm to 5 µm is between about 80% and about 85%. In some embodiments, the percentage of particles having diameters within the range of 0.5 µm to 5 µm is between about 85% and about 90%. In some embodiments, the percentage of particles having diameters within the range of 0.5 µm to 5 µm is between about 90% and about 95%. In some embodiments, the percentage of particles having diameters within the range of 0.5 µm to 5 µm is between about 95% and about 99.5%. The higher the concentration of particles having particle diameters in the range of 0.5 µm to 5.0 µm, the greater the rate of ethanol absorption into the blood flowing through the lungs, and the faster pain relief is achieved. Particles having diameters larger than about 5 µm are sufficiently large to impact the bronchial tissue during travel from the nebulizer to the alveoli in the lungs, and thus are not absorbed as efficiently as particles having diameters in the range of 0.5 µm to 5 µm. In a plume of particles, the larger the concentration of particles with diameters in the range of 0.5 µm to 5 µm, the less ethanol solution is used to achieve pain relief, and the patient replaces the ethanol solution less often, increasing the likelihood of patient adherence to a pain relief treatment plan. In some embodiments, the percentage of particles having diameters within the range of 0.5 µm to 5 µm is between about 40% and about 80%, and the dose size is scaled to account for the particle distribution range to achieve a total number of particles having a diameter within the range of 0.5 µm to 5 µm according to the particle distributions described above (wherein, pain relief is triggered by the brain effect of the inhaled "small particle" ethanol solution with diameters of 0.5 µm to 5 µm, and the remainder of ethanol solution impacts on nasal or lung tissue without being absorbed into the bloodstream).

In some embodiments, the active mesh nebulizer is configured to deliver the first dose of ethanol to the patient, and then to lock out (or prevent) functioning of the active mesh in order to prevent overdosing by the patient after delivery of the first dose of ethanol. In some embodiments, the active mesh nebulizer unlocks functioning of the active mesh upon expiration of a dose delay period (e.g., a regular interval), when a subsequent first dose of ethanol is to be provided according to the alcohol treatment in the pain regulation plan. In some embodiments, the dose delay period is about 24 hours. In some embodiments, the dose delay period is between about 3 hours and about 12 hours. In some embodiments, the dose delay period is about 4 hours to about 8 hours. Dose delay periods greater than about 24 hours are more likely to be associated with patients with mild pain experiencing the return of pain symptoms due to, e.g., the synergistic effect of the nebulized ethanol interacting with opioid medications. For patients experiencing stronger pain levels, dose delay periods larger than about 12 hours are more likely to be associated with patients experiencing the return of pain symptoms. Patients experiencing stronger pain are likely to see pain symptoms recur at shorter intervals, and thus shorter dose delay periods are used to achieve pain relief for such patients. In some embodiments, the dose delay period is customized according to a patient's individual response to alcohol metabolism and alcohol symptoms.

In operation 112 of method 100, as part of the pain regulation plan, the patient pain level is measured after a monitoring period (e.g., weekly, or every two weeks, or monthly, or quarterly, and so forth), to determine whether the first dose of ethanol delivered to the patient according to operation 110 has effectively brought pain relief. A monitoring period is adjusted according to a patient convenience, or in response to a reported pain level change of the patient. In some embodiments, patients report complete pain relief after a single delivery of the first dose of ethanol. In some embodiments, at the end of the monitoring period, the pain level change is an increase in pain. In some embodiments, at the end of the monitoring period, the pain level change is a decrease in pain. Pain level increases after the monitoring period ends are associated with a change in the underlying medical condition which results in increased pain, leading to, e.g., a determination to increase the delivered dose of ethanol to achieve pain relief and further medical care (e.g., to replace the first dose of ethanol with a second dose of ethanol which is larger than the first dose of ethanol). Pain level decreases after the monitoring period ends are associated with an effective dose of nebulized ethanol, and, e.g., a determination to maintain the dose of nebulized ethanol, or to decrease the dose of nebulized ethanol to test the patient response for similar pain relief with smaller doses.

In operation 114 of method 100, the patient pain level is evaluated. In some embodiments, evaluating the patient pain level includes comparing the current pain level measurement to the pain level measured in operation 102, at the start of the pain regulation plan. In some embodiments, evaluating patient pain level includes comparing the current pain level measurement to a prior pain level after ethanol treatment has begun (e.g., after repeating performing operation 110).

In operation 116 of method 100, a determination is made regarding whether patient status (e.g., patient pain experience) indicates changing the ethanol dose or the dose of any other pain medication that a patient is taking is indicated.

When the evaluation of patient pain level (see operation 114) and determining whether patient behavior indicates changing the ethanol dose (operation 116), the operation proceeds to operation 104 to determine a new dose of ethanol.

When the evaluation of patient pain level (see operation 114) and determining whether patient behavior does not indicate changing the ethanol dose or the dose of another pain medication the patient is taking (see operation 116), the method proceeds to operation 118 and the patient continues to receive treatment as before.

When the evaluation of patient pain level (see operation 114) and determining whether patient behavior indicates that changing the ethanol dose is advised (see operation 116), the method proceeds to operation 104 and a new ethanol dose is determined.

When the evaluation of patient pain level (see operation 114) and determining whether patient behavior indicates changing the dose of another pain medication the patient is taking (see operation 116), the method proceeds to operation 117.

The determination is made by performing, e.g., a patient survey regarding pain levels, sleep habits, sleep disturbance, patient alertness, patient mobility, and, in some instances, the results of decreasing a dose of other pain relief medications consumed by the patient during the use of the active mesh nebulizer to accomplish pain relief with ethanol solutions. In some embodiments, the determination is performed on a weekly basis, a monthly basis, or on an as-needed basis in response to a patient's report of changes in the sensation or severity of pain over a span of time, or a change in side effects caused by the other analgesic compounds taken by the patient, as described above. In some embodiments, the determination is repeated at a regular interval (e.g., quarterly, or semi-annually) to maintain a patient's pain relief and increase opportunities to decrease the dosage of other pain relief medications consumed by the patient.

In operation 117, a new dose of a pain medication other than the delivered alcohol is determined by, e.g., a health care provider, and the method continues to operation 118, wherein the ethanol dose, as determined in operation 110, is delivered to the patient as before.

In some embodiments, a dose of ethanol taken by a patient remains constant throughout a pain management plan. In some embodiments, the dose of ethanol taken by a patient changes throughout a pain management plan. In some embodiments, the ethanol dose increases as the patient initiates pain level reduction, and decreases once a predetermined pain level has been obtained. In some embodiments, the ethanol dose remains constant until a patient has experienced two or more consecutive pain measurements with the same pain level, at which time the ethanol dose is changed (increased or decreased). In some embodiments, the dose of ethanol remains constant and the doses of other pain medications taken by the patient are changed in order to reduce side effects of the other pain medications and improve patient quality of life.

In operation 118 of method 100, the dose of ethanol is delivered to the patient as described above in operation 110 until a monitoring period has elapsed, and the method 100 continues with operation 112.

According to some embodiments, pain relief experienced by patients using nebulized ethanol appears to last for between 3 and 4 hours. In persons who partake of nebulized alcohol in the absence of significant pain, the brain effects of the nebulized alcohol (euphoria, and so forth) appear to last about 2 hours. Persons who take nebulized alcohol for pain report feeling moderate sleepiness or drowsiness, but not "buzzed" or "intoxicated".

Treatment Examples

The following is a set of non-limiting examples of patient treatment envisioned within the scope of the present disclosure in order to achieve pain relief for a patient. A person having ordinary skill in the art will understand and anticipate that the following examples do not limit the scope of the pain relief which is achievable by the method described herein.

Example 1: A first patient treatment example is that of an adult male experiencing pain from multiple neck injuries and replaced vertebrae who was treating pain using 60 mg Oxycontin® (30 mg in morning and night) and 6 doses of Percocet® daily as needed before ethanol treatment. The patient's opioid usage history spanned 11 years. The first patient also took Ambien® at night to promote sleep. Over the course of ethanol treatment, the patient exhibited significantly lower reported levels of pain, improved physical stamina, physical performance (kidney and bowel function), and mental acuity, and reduced opioid usage.

The first patient takes nebulized alcohol in the morning and at bedtime (about 3-4 inhalations each time), wakes in the night to use the bathroom, and occasionally takes nebulized alcohol during the night. The patient reports reduced usage of sleep aids to counteract discomfort and pain from injuries, and increased quality of sleep.

The first patient reports that over 6 months of ethanol therapy from an active mesh nebulizer as described herein, Oxycontin® usage has been reduced to 10 mg/day, taken in the morning, and no Percocet® during the day.

The first patient reports the following results from reduced Oxycontin® doses: [1] increased renal function (no more water retention/bloating), [2] increased bowel function, [3] greater mobility (able to resume dance activities), [4] improved posture (able to hold head in a vertical position), and [5] increased alertness, attention, and mental acuity.

Example 2: A second patient treatment is of an adult experiencing sinus headaches using nebulized ethanol solution. The second patient takes 1-2 inhalations of nebulized ethanol and achieves pain relief at a significantly faster rate than other treatments (sinus rinse, other pain medications).

Example 3: A third patient experienced acute pain from a chronic back injury which occurred during a car accident approximately 40 years earlier. The patient experienced acute pain for about 8 hours, requiring assistance to lower himself to sit in a chair, to stand up from the chair, and to walk about. The patient used ethanol therapy as described herein (at a rate of 5 inhalations per treatment) to achieve complete pain relief from the chronic back injury. The patient reported that pain recurred approximately 12 hours after the initial session of ethanol therapy, at which time he repeated the treatment (at a rate of 4 inhalations per treatment) for complete relief from pain symptoms. The third patient reported complete remission of pain in 48 hours, approximately 50% of the length of time previously associated with remission of the pain using other analgesics prior to ethanol therapy.

Example 4: The following is a non-limiting example of treating a patient with nebulized ethanol using an active mesh nebulizer. An active mesh nebulizer is configured to deliver ethanol solution to a patient at a rate of 0.2 ml/minute. A patient inhales a plume of particles from the active mesh nebulizer for a total of five inhalations, wherein, for each inhalation, the active mesh of the active mesh nebulizer vibrates for about 3 seconds. Thus, a patient is treated to achieve a state of pain relief with a dose of 0.05 ml ethanol solution (see equation 1), below:

$$\left(\frac{0.2 \text{ ml ethanol solution}}{\text{minute}}\right)\left(\frac{1 \text{ minute}}{60 \text{ seconds}}\right) \quad \text{Equation (1)}$$

$$\left(\frac{3 \text{ seconds}}{1 \text{ inhalation}}\right)(5 \text{ inhalations}) = 0.05 \text{ ml ethanol solution}$$

In an embodiment of the method where the ethanol solution is 100% ethanol, the ethanol dose is thus 0.05 ml ethanol. In an embodiment of the method where the ethanol solution is 75% ethanol, the ethanol dose is thus 0.75×(0.05 ml)=0.0375 ml ethanol. In an embodiment of the method where the ethanol solution is 25% ethanol, the ethanol dose is thus 0.0125 ml ethanol.

Figure 2:
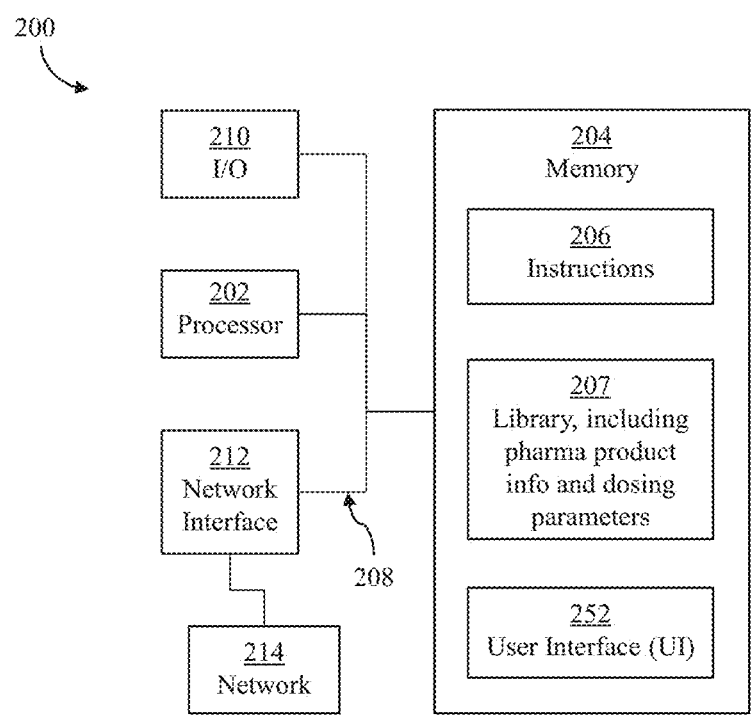
FIG. 2 is a block diagram of a computer system in accordance with some embodiments.

FIG. 2 is a block diagram of a computer system 200 in accordance with some embodiments.

In some embodiments, computer system 200 is a general purpose computing device including a hardware processor 202 and a non-transitory, computer-readable storage medium (storage medium) 204. Storage medium 204, amongst other things, is encoded with, i.e., stores, computer program code 206, i.e., a set of computer-executable instructions (instructions). Execution of instructions 206 by hardware processor 202 (e.g., a controller) represents (at least in part) a controller which implements a portion or all of the various operations of embodiments of method 100 described herein.

Hardware processor 202 is electrically coupled to computer-readable storage medium 204 via a bus 208. Hardware processor 202 is also electrically coupled to an I/O interface 210 by bus 208. A network interface 212 is also electrically connected to hardware processor 202 via bus 208. Network interface 212 is connected to a network 214, so that hardware processor 202 and computer-readable storage medium 204 are capable of connecting to external elements via network 214. Hardware processor 202 is configured to execute computer program code 206 encoded in computer-readable storage medium 204 in order to cause computer system 200 to be usable for performing a portion or all of the noted operations and/or methods. In one or more embodiments, hardware processor 202 is a central processing unit (CPU), a multi-processor, a distributed processing system, an application specific integrated circuit (ASIC), and/or a suitable processing unit.

In one or more embodiments, computer-readable storage medium 204 is an electronic, magnetic, optical, electromagnetic, infrared, and/or a semiconductor system (or apparatus or device). For example, computer-readable storage medium 204 includes a semiconductor or solid-state memory, a magnetic tape, a removable computer diskette, a random access memory (RAM), a read-only memory (ROM), a rigid magnetic disk, and/or an optical disk. In one or more embodiments using optical disks, computer-readable storage medium 204 includes a compact disk-read only memory (CD-ROM), a compact disk-read/write (CD-R/W), and/or a digital video disc (DVD).

In one or more embodiments, storage medium 204 stores computer program code 206 configured to cause computer system 200 to be usable for performing a portion or all of the noted operations and/or embodiments of the method 100. In one or more embodiments, storage medium 204 also stores information which facilitates performing a portion or all of the noted operations and/or methods. In one or more embodiments, storage medium 204 stores a library 207 of pharmaceutical product information and dosing parameters for patients and users of active mesh nebulizers, according to patient age, patient weight, patient sex, and other parameters which relate to patient sensitivity and responsiveness to doses of pharmaceutical products delivered by active mesh nebulizer.

Computer system 200 includes I/O interface 210. I/O interface 210 is coupled to external circuitry. In one or more embodiments, I/O interface 210 includes a touchscreen, and/or cursor direction keys for communicating information and commands to hardware processor 202.

In some embodiments, computer system 200 also includes network interface 212 coupled to hardware processor 202. Network interface 212 allows computer system 200 to communicate with network 214, to which one or more other computer systems are connected. Network interface 212 includes wireless network interfaces such as BLUETOOTH, WIFI, WIMAX, GPRS, or WCDMA; or wired network interfaces such as ETHERNET, USB, or IEEE-1364. In one or more embodiments, a portion or all of noted processes and/or methods, is implemented in two or more COMPUTER systems 200.

Computer system 200 is configured to receive information through I/O interface 210. The information received through I/O interface 210 includes one or more of instructions, data, design rules, libraries of standard cells, and/or other parameters for processing by hardware processor 202. The information is transferred to hardware processor 202 via bus 208. Computer system 200 is configured to receive information related to a UI through I/O interface 210. The information is stored in computer-readable medium 204 as user interface (UI) 252.

In some embodiments, a portion or all of the noted processes and/or methods is implemented as a standalone software application for execution by a processor. In some embodiments, a portion or all of the noted processes and/or methods is implemented as a software application that is a part of an additional software application. In some embodiments, a portion or all of the noted operations and/or methods is implemented as a plug-in to a software application.

In some embodiments, the processes are realized as functions of a program stored in a non-transitory computer readable recording medium. Examples of a non-transitory computer readable recording medium include, but are not limited to, external/removable and/or internal/built-in storage or memory unit, e.g., one or more of an optical disk, such as a DVD, a magnetic disk, such as a hard disk, a semiconductor memory, such as a ROM, a RAM, a memory card, and the like.

The instructions for the active mesh nebulizer relate to parameters associated with operating the active mesh nebulizer to deliver a plume of particles to a patient or user, to determine the total dose of the medication in the ethanol solution for a patient or user's care, and/or the timing associated with operating the active mesh to deliver medications to the patient or user. An active mesh nebulizer has an active mesh, a sheet of material (metal or a polymer) having holes therein and connected to a piezoelectric element. During plume generation, the active mesh is in direct contact with the ethanol solution while a controller starts and stops vibration of the active mesh, or starts and stops the piezoelectric element connected to the active mesh. Plume generation occurs during mesh vibration, resulting in liquid being forced through the holes in the active mesh and into a volume of air (for example within a mouthpiece) where the particles are positioned for inhalation. By directing the plume of particles toward a patient mouth (e.g., by directing the particles into the mouthpiece volume prior to or during inhalation), the generated particles are absorbed into the lungs during inhalation, with no waste. By ending the plume generation prior to the end of an inhalation, the entirety of the plume is absorbed by the patient through the lungs and no liquid, or chemical compound in the liquid, is wasted. In some embodiments, the active mesh vibration starts after a patient or user inhales, and stops before a patient or user stops the inhalation. In some embodiments, the instructions for the active mesh nebulizer determine a duration of a vibration period during a patient or user inhalation to prevent waste of the ethanol solution in an un-inhaled plume of particles.

In some embodiments, based on the instructions provided to an active mesh nebulizer, as described in U.S. patent application Ser. No. 17/100,566 titled "NEBULIZER DELIVERY SYSTEMS AND METHODS" and filed on Nov. 20, 2020, the active mesh nebulizer includes instructions (see computer program code 206) configured to determine, based on a size of a dose of pharmaceutical compound, or ethanol, a duration of a total vibration period to deliver a full dose of medication (e.g., ethanol) to a patient or user. In some embodiments, a controller (see, e.g., hardware processor 202) is configured to perform the calculation of the total vibration time of the active mesh nebulizer. In some embodiments, the controller is configured to read dose information from a programmed storage unit which accompanies a vial of the ethanol solution. In some embodiments, the controller is configured to request and receive dose information over a network before calculating the vibration time to deliver the dose of the ethanol solution. A full dose of medication is a quantity prescribed for periodic delivery to the patient or user by the medical provider. In some embodiments, according to a concentration of medication (a single compound, or a mixture of multiple compounds) in the ethanol solution, the total vibration period to deliver the full dose of medication to the user is shorter than a duration of a single patient inhalation. The total vibration period to deliver a full dose of medication is based on the characterized nebulization rate of the active mesh, the viscosity of the ethanol solution, the quantity of liquid in contact with the mesh (e.g., the coverage area of the liquid on the active mesh) during mesh vibration, the patient or user lung volume, the lung inflation rate for the patient or user, the absorptive surface area of the lung (which may be compromised by medical conditions such as emphysema), and so forth. During operation of an active mesh nebulizer, nebulization rate is a function of at least the active mesh vibration rate, the diameter and number of holes in the mesh, and the voltage applied to the piezoelectric vibrating element. Droplet formation by the active mesh is a function of the ethanol solution viscosity. In some embodiments, a mesh produces an acceptable plume of particles for inhalation into the lungs for a range of ethanol solution viscosities, and a different active mesh is indicated to produce plumes of particles of ethanol solutions having a viscosity outside the range of the initial active mesh performance specification. Mesh coverage area also relates to the rate of plume generation. When an entirety of the active mesh is in contact with a ethanol solution, the nebulization/plume generation rate is greater than during operation of the active mesh having only half of the active mesh in contact with the ethanol solution. Plume generation efficiency, and dosing accuracy, is improved by an active mesh nebulizer configured to promote greater amounts of mesh coverage by the ethanol solution. Plume generation rates are a function of the vibrational frequency of the piezoelectric vibrating element. In some embodiments, increasing the voltage applied to the piezoelectric vibrating element increases the vibrational frequency of the piezoelectric vibrating element and the rate of particle production.

In some embodiments, the instructions include a programmed total dose of medication for a patient or user, and the total vibration period is determined by dividing the total dose by the nebulization rate of the active mesh nebulizer. In embodiments of the method where the total vibration period is longer than the inhalation period of which a patient or user is capable (due to, e.g., physiological constraints), or expected of a patient or user (due to, e.g., age of the user, or mental capacity), the total vibration period is divided into smaller sub-dose vibration periods and the total dose of medication is provided to the patient or user over multiple inhalations. In embodiments of the method where the total vibration period is less than the inhalation period of which a patient or user is capable (due to, e.g., physiological constraints), or expected of a patient or user (due to, e.g., age of the user, or mental capacity), the total dose of medication is provided to the patient or user in a single inhalation period.

In some embodiments, the patient is alerted to begin inhalation in order to receive a total dose, or a sub-dose, of medication, i.e., the ethanol solution. In some embodiments, the patient alert comprises a vibration of the active mesh nebulizer while the patient or user holds the nebulizer against the patient or user's mouth for inhalation. In some embodiments, the patient alert comprises a sound or tone generated to alert the user to begin inhalation. In some embodiments, the patient alert comprises a visual alert (e.g., a blinking light or visual indicator) to begin inhalation. In some embodiments, the patient alert is provided by the active mesh nebulizer. In some embodiments, the patient alert is provided by a computing device communicatively connected to the active mesh nebulizer to facilitate patient treatment and/or active mesh nebulizer operation. Examples of a computing device communicatively connected to the active mesh nebulizer include a dedicated nebulizer controller unit, a "smartphone," a "feature-rich" phone, a computing tablet, or any other kind of computing device configured with software instructions and a communication channel to communicate with the active mesh nebulizer and interact with the patient or user. In some embodiments, the patient alert comprises at least two of more of a sound, a vibration (tactile alert), or a visual alert of the active mesh nebulizer and/or the connected computing device.

According to theory and belief, a patient inhalation typically ranges from about three (3) seconds to about ten (10) seconds before a patient has inhaled sufficient air to inflate the lungs to a maximum lung volume. In some embodiments, inhalation may occur over timespans ranging from 10 seconds to 20 seconds, and the slower rate of inhalation is believed to have an impact on the distribution of inhaled particles in the lungs, and on the absorption rate of the medication. In some embodiments, the amount of time a patient or user is able to inhale is influenced by lung volume, bronchial diameter, and so forth.

In some embodiments, patient age or mental capacity of a patient is a factor in the amount of time a patient or user is able to inhale, and/or the spacing between inhalation periods. For young patients, or patients with cognitive impairment, spacing between inhalation periods to deliver a dose of medication is longer than for adults or patients with no cognitive impairment in order to provide the patient an opportunity to prepare for a possible second inhalation period for a multi-inhalation medication delivery scenario. According to some embodiments, the instructions are configured to scale the duration of the inhalation period based on (e.g., approximately proportional to) the patient lung volume, as compared to a patient having no physiological impairment. In some embodiments, instructions to the active mesh nebulizer for determining a total number of inhalation periods of an active mesh nebulizer are adjusted according to the age and gender of the patient or user, the measured lung volume of the patient, the peak flow (during exhalation) measurement of a patient or user, or other physiological factors such as surgical history (e.g., whether portions of the lungs have been removed), heart volume, patient weight, fluid buildup around the heart or lungs, and the like.

In some instances, the instructions include a programmable vibration start delay period between the start of an alert to a patient to begin inhalation, an end of the patient alert, or some other factor associated with timing of inhaling the plume of particles. According to some embodiments, the duration of a programmable vibration start delay period ranges from about 1 second to about 3 seconds. Vibration start delay periods shorter than about 1 second are believed more likely to result in wasted plume than for longer delay periods. Vibration start delay periods longer than about 3 seconds are believed to be, for most patients, of such length that the patient has begun inhaling before the plume is generated, inflating the lungs with air that does not contain particles of ethanol solution of the medication, making inhalation of the whole plume of particles more difficult. While some patients are expected to find such vibration start delay periods unacceptable (e.g., uncomfortable or inconvenient), the net result is to increase a number of inhalation periods to deliver a full dose of medication. For patients with cognitive impairment, or young patients, a vibration delay period of about 3 seconds, or longer, is appropriate to accommodate the different response time or concentration the patient or user is able to pay to the treatment process. The vibration start delay period is intended to be programmable by a medical provider or other person monitoring performance of the patient or user such that the patient or user becomes habituated to a customized treatment process adapted to the patient or user's individual ability. Successful adaptation of the patient or user creates an opportunity for patient self-medication for some medications, without constant oversight by a medical provider.

The process of generating the plume of particles is halted before the patient stops the inhalation in order to avoid wasting the medication in the un-inhaled ending portion of the plume of particles. According to some embodiments, the patient is signaled as to the duration of the inhalation period by an alert from the active mesh nebulizer, or a connected computing device. In some embodiments, the patient is provided a periodic alert to track or count to indicate continuing plume generation and avoid inadvertent wasting of a last portion of the plume of particles. In some embodiments, the patient is provided an "ending" alert, different from a starting alert, and/or different from a "tracking" or "counting" alert, to indicate that the plume generation has halted. In some embodiments, a patient is provided an alert (a "further inhalation" alert) to indicate that further inhalation periods are upcoming to prepare for additional plume generation. In some embodiments, a patient is provided an alert (a "final" alert) to indicate that the total dose of medication has been delivered and no further inhalations are upcoming until another full dose of medication is scheduled. In some embodiments, the alerts are tones, vibrations, visual alerts, or recorded messages indicating a status of the active mesh nebulizer or a treatment status (a number of sub-doses delivered, a number of sub-doses remaining, an anticipated number of doses remaining in the vial, and so forth). "Coordinating" alerts to guide a patient or user to start, maintain, or halt inhalation around the programmed generation of the plume of particles are customizable according to the patient's ability to process and adhere to a treatment protocol, and are used singly, or in combination, in order to achieve patient compliance with treatment.

In some embodiments, the active mesh nebulizer controller determines whether the dose of medication has been delivered according to the instructions received by the active mesh nebulizer. Upon determining that the total dose of medication has not been delivered, the method repeats the plume generation after a short delay. Upon determining that the total dose of medication has been delivered, the active mesh nebulizer performs a lockout function to prevent accidental overdosing. In some embodiments, the active mesh nebulizer operates under a "fixed dosage" model and is halted until a full dose delay period expires, when an additional full dose of medication is delivered from the active mesh nebulizer in one or more inhalations. In "fixed dosage" operation, the halt between treatment by the active mesh nebulizer is complete and no intermediate operation is allowed (see, e.g., partial dosing, or "running" dosing, below). In some embodiments, the active mesh nebulizer operates under a "partial dosage" model and, upon completion of a full dose of medication, is completely halted until a partial dose delay period expires, at which time the active mesh nebulizer activates to delivery of a partial dose of medication, but not a full dose of medication. In "partial dosage" operation, the nebulizer becomes available for a treatment with a partial dose of medication from the expiration of the partial delay period until the expiration of the full dose delay period, at which point the nebulizer becomes available for treatment with a full dose of medication.

In some embodiments, the active mesh nebulizer operates a "running dosage" model, wherein the active mesh nebulizer remains available for additional treatment with the medication at all times, unless an additional partial or full treatment of medication will exceed a blood serum concentration, or some other physiological threshold, of the medication in the patient or user. As the amount of delivered medication approaches a calculated blood serum concentration (threshold, especially for tissue toxicity or other adverse effect), the nebulizer completely halts operation until such time as the calculated blood serum concentration, or other physiological threshold, will not be exceeded by an additional partial or full dose of medication. A mode of delivery of medications from the active mesh nebulizer is a function of the chemical nature of the medication, the patient's metabolic ability with regard to the medication, and the patient's sensitivity to the medication, among others. The instructions of the nebulizer are configured to account for the aforementioned factors to avoid over dosage or other adverse patient outcomes based on taking the medication.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method, comprising:

measuring a patient pain level prior to delivering a dose of analgesic compound to the patient;

determining a number of inhalation periods in which to deliver the dose of analgesic compound to the patient;

delivering the dose of analgesic compound to the patient by inhalation by the patient from an active mesh nebulizer at a regular interval, wherein delivering the dose of analgesic compound to the patient is delayed by 1 to 3 seconds after the patient initiates inhalation;

measuring the patient pain level after delivering the dose of analgesic compound to the patient; and determining whether to repeat delivering the dose of analgesic compound to the patient, wherein the dose of analgesic compound comprises a dose of ethanol, the dose of analgesic compound delivered by inhalation from the active mesh nebulizer further comprises particles having a diameter of not less than 0.5 μm and not greater than 5 μm, and wherein delivering the dose of analgesic compound to the patient begins to provide pain relief within about 10 seconds.

2. The method of claim 1, wherein delivering the dose of ethanol to the patient by inhalation from an active mesh nebulizer at a regular interval further comprises:

generating a plume of particles of an ethanol solution in the active mesh nebulizer after the start of a patient inhalation; and stopping generating the plume of particles of the ethanol solution before the end of the patient inhalation.

3. The method of claim 2, further comprising:

calculating a vibrational time for the active mesh of the active mesh nebulizer to generate the dose of ethanol based on an active mesh nebulizer nebulization rate, an alcohol concentration in the ethanol solution, and the dose of ethanol.

4. The method of claim 3, further comprising monitoring the vibrational time of the active mesh and preventing the active mesh from vibrating upon reaching the calculated vibrational time to generate the dose of ethanol.

5. The method of claim 1, further comprising:

evaluating the patient for symptoms of alcohol intolerance subsequent to delivering the dose of ethanol to the patient by inhalation from the active mesh nebulizer.

6. The method of claim 5, further comprising:

determining the dose of ethanol by delivering at least one incremental dose of ethanol from the active mesh nebulizer until the patient exhibits symptoms of alcohol intolerance.

7. The method of claim 6, wherein the dose is the at least one incremental dose of ethanol multiplied by a scaling factor ranging from 0.5 to 0.8.

8. The method of claim 1, further comprising determining whether to change the dose of ethanol delivered by inhalation from the active mesh nebulizer.

9. A method, comprising:

measuring a patient pain level;

determining a first dose of ethanol by scaling a cumulative dose of ethanol;

delivering the first dose of ethanol to a patient by inhalation from an active mesh nebulizer at a repeated interval;

evaluating the patient pain level after delivering the first dose of ethanol to the patient by inhalation from the active mesh nebulizer at a repeated interval;

determining whether to replace the first dose of ethanol with a second dose of ethanol different from the first dose of ethanol; and delivering the second dose of ethanol to a patient by inhalation from the active mesh nebulizer at the repeated interval, wherein delivering a dose of ethanol to a patient by inhalation from an active mesh nebulizer further comprises delivering droplets of ethanol solution having a diameter of not less than 0.5 µm and not greater than 5 µm, wherein each of delivering the first dose of ethanol and delivering the second dose of ethanol begins to provide an analgesic effect within about 10 seconds from delivering the dose of ethanol.

10. The method of claim 9, further comprising:

determining, subsequent to delivering the second dose of ethanol to the patient by inhalation from the active mesh nebulizer at the repeated interval, whether to replace the second dose of ethanol with a third dose of ethanol, wherein the third dose of ethanol is larger than the second dose of ethanol.

11. The method of claim 9, further comprising:

determining, for a patient taking a non-alcohol pain medication, whether to adjust a first dose of the non-alcohol pain medication while continuing to deliver the second dose of ethanol at the repeated interval to the patient taking the non-alcohol pain medication.

12. The method of claim 11, further comprising:

replacing the first dose of the non-alcohol pain medication with a second dose of the non-alcohol pain medication and continuing to deliver the second dose of ethanol to the patient by inhalation from the active mesh nebulizer at the repeated interval.

13. A method of reducing patient pain, comprising:

determining a degree of patient pain in a patient;

delivering a dose of analgesic compound to the patient, wherein the analgesic compound further comprises ethanol, and wherein delivering the dose of analgesic compound further comprises delivering the ethanol to the patient from an active mesh nebulizer at a regular interval after determining the degree of patient pain in the patient, wherein delivering the dose of analgesic compound begins to provide an analgesic effect within about 10 seconds from delivering the dose of analgesic compound;

measuring the degree of patient pain after delivering the dose of analgesic compound to the patient from the active mesh nebulizer; and determining whether to repeat delivering the dose of analgesic compound to the patient from the active mesh nebulizer.

14. The method of claim 13, wherein delivering a dose of analgesic compound to the patient from the active mesh nebulizer at a regular interval further comprises:

generating a plume of particles of an ethanol solution in the active mesh nebulizer; and inhaling the plume of particles of the ethanol solution.

15. The method of claim 14, wherein generating a plume of particles of an ethanol solution further comprises generating a plume of particles, wherein at least 80% of the particles have a particle diameter of at least 0.5 micrometers (µm) and not more than 5.0 µm.

16. The method of claim 14, wherein delivering the dose of analgesic compound to the patient from the active mesh nebulizer at a regular interval further comprises delivering the dose of analgesic compound at a regular interval of not more than 12 hours.

17. The method of claim 13, further comprising evaluating the degree of patient pain after delivering the dose of analgesic compound; and determining whether to modify the dose of analgesic compound in response to evaluating the degree of patient pain.

18. The method of claim 17, further comprising:

delivering a dose of non-alcohol pain medication to the patient; and determining, for a patient taking the non-alcohol pain medication after delivering the dose of analgesic compound from the active mesh nebulizer, whether to adjust a dose of the non-alcohol pain medication while continuing to deliver the dose of analgesic compound at the regular interval to the patient taking the non-alcohol pain medication.

19. The method of claim 18, further comprising adjusting the dose of the non-alcohol pain medication in response to determining whether to adjust the dose of the non-alcohol pain medication.

20. The method of claim 17, further comprising monitoring the dose of analgesic compound delivered from the active mesh nebulizer by monitoring a duration of vibrational time for the active mesh in the active mesh nebulizer.

* * * * *